United States Patent [19]

Shoesmith

[11] Plant 4,509

[45] Mar. 11, 1980

[54] CHRYSANTHEMUM NAMED GETTYSBURG

[75] Inventor: Leonard H. Shoesmith, Westfield-Woking, England

[73] Assignee: Pan-American Plant Company, West Chicago, Ill.

[21] Appl. No.: 955,003

[22] Filed: Oct. 26, 1978

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new variety of chrysanthemum plant characterized by its single flower form having intense yellow ray florets, of which there are several rows, possessing good substance and long life. This new plant is not temperature sensitive and can be flowered the year around on medium treatment producing abundant blooms of medium size with minimal pollen production when grown as a spray pot plant.

2 Drawing Figures

BACKGROUND OF THE NEW PLANT

This chrysanthemum plant originated as a seedling of unknown parentage grown from seeds of random pollinated plants maintained by me at Westfield-Woking, Surrey, England, for chrysanthemum discovery purposes. This plant was discovered by me in 1974 and was asexually reproduced by me at said Westfield-Woking by means of cuttings from the original plant with the object of determining its suitability for commercial scale propagation. Several successive generations of this new variety, propagated by means of vegetative cuttings, have demonstrated that its distinguishing characteristics hold true from generation to generation and appear to be firmly fixed and propagation of the plant by vegetative cuttings is now being done for commerical purposes at West Chicago, Ill., and at Cortez, Fla.

DESCRIPTION OF THE DRAWINGS

This new variety of chrysanthemum plant is illustrated by the accompanying drawings; the first drawing is a hand painted drawing showing face views of several flowers to show the true flower colors; and the other drawing is a mechanical reproduction of a Xerographic copy of representative leaves of this new chrysanthemum plant.

DESCRIPTION OF THE NEW PLANT

The following is a detailed description of my new chrsyanthemum variety with color designations according to The R.H.S. Colour Chart published by The Royal Horticultural Society of London, England, the observations having been made of greenhouse cultured plants grown at West Chicago, Ill. in the Spring months of 1978.

THE PLANT

Origin: Seedling

Parentage: Unidentified random pollinated chrysanthemum plants.

Classification:

*Botanic.*—*Chrysanthemum morifolium.*

*Commercial.*—Greenhouse pot plant.

Form: Perennial herbaceous bush.

Height: About 29 to 39 cm.

Growth: Vigorous, upright and terminal, somewhat spreading with good strength and sturdiness.

Branching: Normal, under natural conditions.

Foliage: Abundant, with about 7 to 9 leaves on 10 cm. inches of stem.

*Leaf size.*—About 5 to 12 cm. long, depending upon age, and about 3 to 7 cm. wide.

*Leaf shape.*—Lobed and deeply cleft and slightly serrated.

*Color.*—Upper side — 137A. Under side — 146A.

*Surface aspect.*—Canescent.

*Venation.*—Pinnate.

*Petioles.*—About 1.0 to 2.6 cm.

THE BUD

Form: Elliptical.

Size: About 1.3 to 1.5 cm. in diameter and about 0.8 to 1.0 cm. in depth.

Opening rate: Slow.

Color:

*When phyllaries divide.*—144A.

*When florets unfurl.*—7A.

Phyllaries: The outside of the receptacle has many spear-shaped and upstanding involucral bracts.

*Color.*—Inside — 137C. Outside 13 137C.

*Surface texture.*—Pubescent.

Peduncle: Erect and about 3.5 to 10 cm. long.

*Surface texture.*—Pubescent.

THE FLOWER

Recommended flowering: Year around.

Response: 9 week.

Natural season: October 21 to 28.

Blooms: Composite and single flower type.

*Size.*—Medium

*Diameter.*—About 5.2 to 7.4 cm.

*Depth.*—About 12 to 15 mm.

*Shape.*—Cup-shaped upon first opening and remaining so through maturity.

*Borne.*—As a head of many florets on a receptacle.

*Florets.*—Numerous in number.

*Form.*—Linear with obtuse apex.

| | | April | May |
|---|---|---|---|
| Color: | Outer floret: | 6A-7A | 5A-6A |
| | Reverse side: | 8A-7B | 8A |
| Disc: | Outer part: | 17A | |
| | Center part: | 144A | |

-continued

| | April | May |
|---|---|---|
| Tonality at 6 feet: | 6A. | |

*Firmness.*—Medium. Appearance: Very slight shine. Discoloration: Slight fade after full bloom.

*Peduncle.*—Upright and sturdy.

*Length.*—3.5 to 10.0 cm.

*Color.*—137C.

Persistence: Florets hang on and dry.

Effect of weather: This plant is recommended for glass house culture only.

Fragrance: Typical chrysanthemum.

Lasting quality: About 3 weeks on the plant. Not recommended for cut flower use.

REPRODUCTIVE ORGANS

Stamens: Anthers — 5 in number, in syngenesious arrangement.

*Filaments.*—About 2 to 5 mm. long.

*Color.*—Light yellow.

*Pollen.*—Color — yellow.

Pistils: Number — one to each ray and disc floret.

*Length.*—About 5 to 7 mm.

*Stigmas.*—Color — yellow.

Ovaries: Inferior bicarpellate.

This new cultivar of pot chrysanthemum is particularly characterized by its single flower form comprising intense yellow ray florets, of which there are several rows, possessing good substance and long life; by its minimal pollen production; and by its medium sized blooms which are abundantly produced when the plant is grown as a spray pot.

This new variety is also characterized by its spreading pot habit, its good breaking ability (making 4 to 6 breaks when manually pinched), its strong stems and its average sized foliage. Also this new plant is not temperature sensitive and can be flowered the year around on medium treatment, flowering 9 weeks after commencement of short days and requiring one 2500 ppm B-9 application during optimum growing periods.

I claim:

1. A new and distinctive cultivar of pot chrysanthemum, substantially as herein shown and described, characterized by its single flower form having intense yellow ray florets possessing good substance and long life, its minimal production of pollen, its abundant production of blooms when grown as a spray pot plant, and its spreading pot habit with good breaking ability.

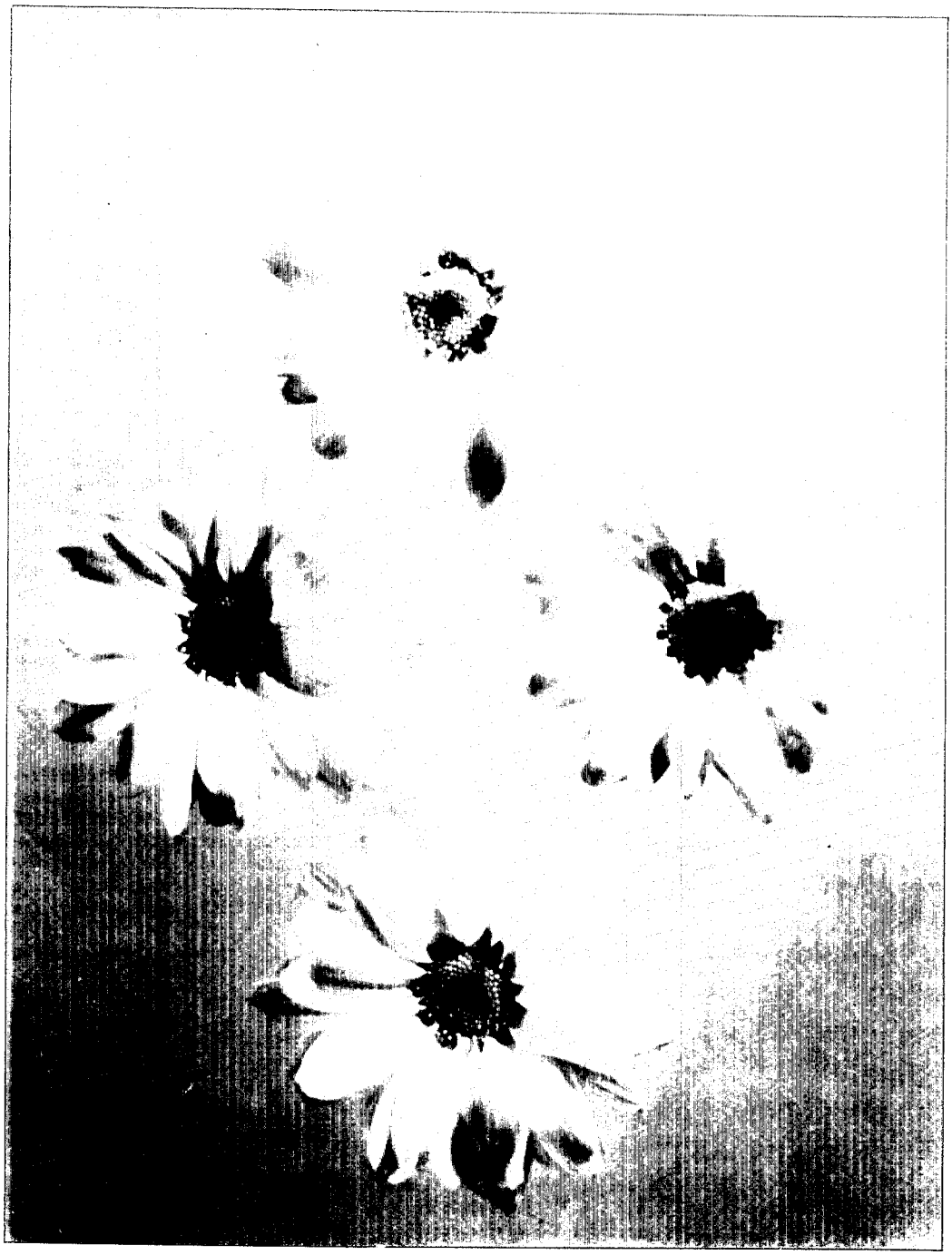

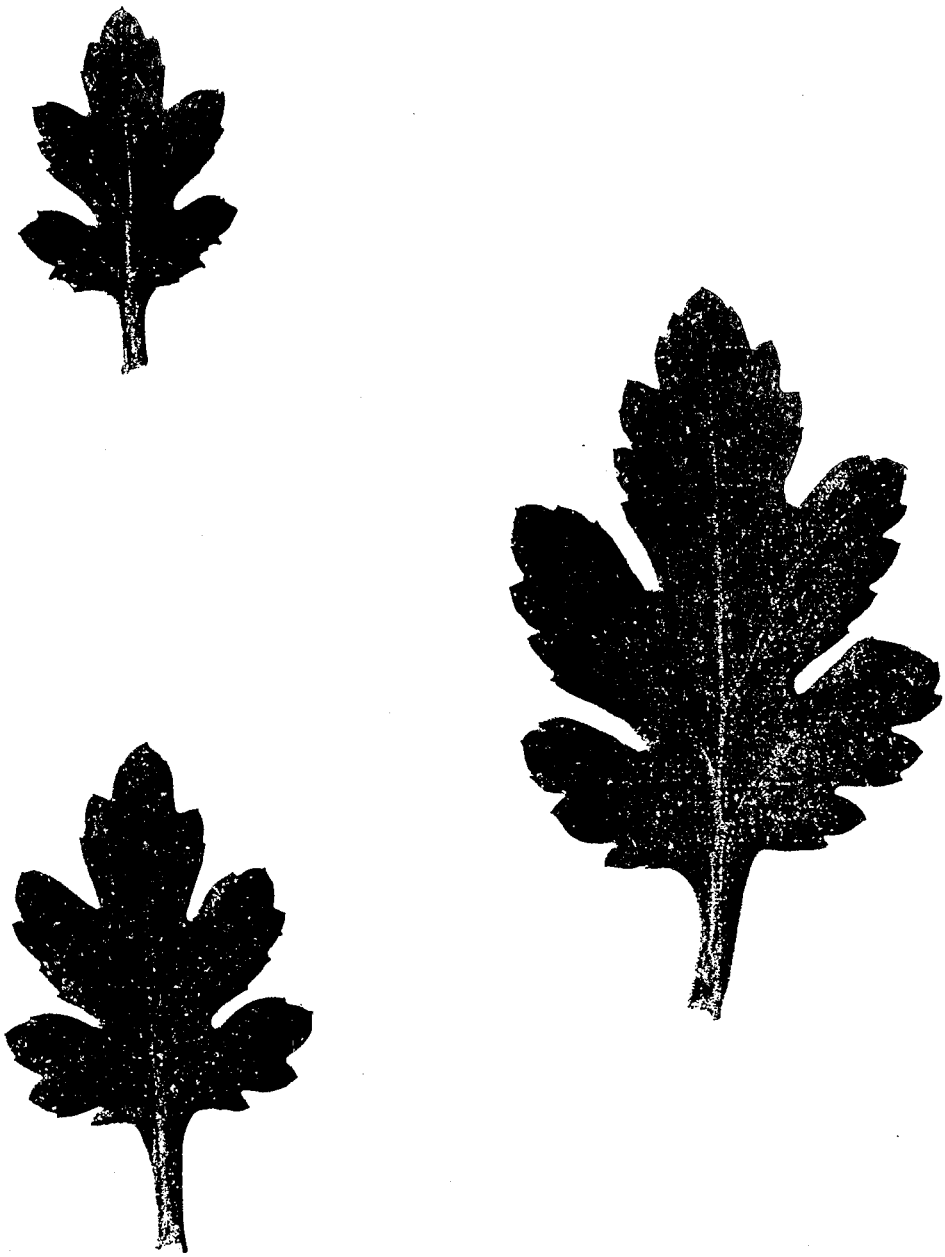

* * * * *